United States Patent
Daggett et al.

[19]

[11] Patent Number: 6,117,095
[45] Date of Patent: Sep. 12, 2000

[54] PORTABLE, ADJUSTABLE, PNEUMATIC, LUMBAR SUPPORT

[76] Inventors: Jonathan G. Daggett; Ronald R. Daggett, both of 111 S. A St., Madera, Calif. 93638

[21] Appl. No.: 09/205,919

[22] Filed: Dec. 4, 1998

[51] Int. Cl.[7] .................................................. A61F 5/00
[52] U.S. Cl. .................................................. 602/19; 602/13
[58] Field of Search .................................. 128/845, 846, 128/847, 869, 870, 871, 877, 882; 602/13, 19, 23, 24; 607/96, 108–112; 5/30, 615, 617, 622, 623, 624, 630, 632, 633, 636, 637, 648, 413 AM, 417, 419, 420, 421, 652

[56] References Cited

U.S. PATENT DOCUMENTS

| | | |
|---|---|---|
| Re. 34,883 | 3/1995 | Grim ........................................ 602/13 |
| 3,974,827 | 8/1976 | Bodeen . |
| 4,135,503 | 1/1979 | Romano . |
| 4,777,346 | 10/1988 | Swanton, Jr. ........................... 219/313 |
| 4,993,409 | 2/1991 | Grim . |
| 5,179,942 | 1/1993 | Drulias et al. . |
| 5,314,235 | 5/1994 | Johnson ................................. 297/284.5 |
| 5,713,841 | 2/1998 | Graham ..................................... 602/32 |
| 5,728,055 | 3/1998 | Sebastian ................................. 602/19 |

*Primary Examiner*—Kim M. Lee
*Attorney, Agent, or Firm*—John D. Gugliotta

[57] ABSTRACT

A portable, adjustable, pneumatic, lumbar support is provided, designed to allow a user with chronic or acute back pain to select and lie in a neutral lumbar position so as to decrease the pain in the lumbar area. When a user is positioned on the present invention, the inflatable bladder extends from the upper portion of the hamstring region of the leg to approximately the L-5 vertebrae, and is constructed such that inflation in the hamstring region causes a displacement greater than that of the buttocks region, allowing for more tilt of the lower spine.

13 Claims, 4 Drawing Sheets

PORTABLE, ADJUSTABLE, PNEUMATIC, LUMBAR SUPPORT

RELATED APPLICATIONS AND DISCLOSURES

The present invention was first disclosed in the Disclosure Document filed on Apr. 9, 1998. There have been no previously filed, nor any co-pending applications, anywhere in the world.

BACKGROUND OF THE INVENTION

1. Field of the Invention

The present invention relates generally to orthopedic supports, and, more particularly, to a portable, adjustable, pneumatic lumbar support.

2. Description of the Related Art

There are a great deal of people who suffer from lower back pain that is derived from a number of sources. Many people suffer from residual pain that began as a result of a previous injury that never completely heals or is easily aggravated. Others suffer from pain that stems from an aggregation of years of improper posturing and insufficient exercise practices.

Regardless of its origin, essential in relieving this pain is the proper positioning of the lumbar vertebrae that make up the portion of the spine, about which most lower back pain occurs. Essential to a healthy lumbar region of the spine, the lumbar vertebrae cannot exhibit an excessive degree of curvature in their vertical orientation in order to ensure that the stress created by the weight of the body is absorbed and transferred vertically through the spine and pelvic region and to the legs.

Typically pain in the lumbar region is caused by an excessive anterior pelvic tilt, a result of poor posture, improper lifting and or obesity, creating an excessive curvature or arching of the lumbar region. Proper alignment of the lumbar lies in a normal position that is located between an anterior pelvic tilt and a posterior pelvic tilt (opposite an anterior tilt).

Conventional treatment of lower back pain caused by improper lumbar curvature consists of a series of pelvic tilt exercises, abdominal strengthening and buttocks strengthening, administered by a physical therapist, doctor, chiropractor and/or physical therapy assistant, followed by the application of a hot pack and/or cold pack or other similar device to the affected region. These pelvic tilt exercises use a variety of positive motion and stretching routines that strengthen the back muscles in the lumbar region and help to train proper lumbar curvature.

Using expensive equipment and services are often effective in relieving lower back pain. However, financial and insurance limitations often prevent these procedures from continuing for an extended period of time and, as a result, the pain can tend to recur.

Accordingly, there is a need for a means by which one can perform pelvic tilt exercises and stretches on their own at home or the office, as part of an exercise regimen or health maintenance routine, without requiring costly services and equipment.

In the related art, several devices are disclosed that describe a back support device with an air bladder, means for inflating it, and a heating element with or without a rheostat. These include U.S. Pat. No. 5,728,055, issued in the name of Sebastian, U.S. Pat. No. 5,179,942, issued in the name of Drulias et. al., U.S. Pat. No. 4,993,409, issued in the name of Grim, U.S. Pat. No. 4,777,346, issued in the name of Swanton and U.S. Pat. No. RE 34,883, issued in the name of Grim.

Several patents disclose a portable orthopedic device with an inflatable bladder. These include U.S. Pat. No. 5,314,235, issued in the name of Johnson, U.S. Pat. No. 4,135,503, issued in the name of Romano and U.S. Pat. No. 3,974,827, issued in the name of Bodeen.

U.S. Pat. No. 5,713,841, issued in the name of Graham describes an inflatable cervical, cervico-thoracic, thoraco-lumbar and a lumbar exercising device.

A search of the prior art did not disclose any patents that anticipate directly many features of the present invention. Consequently, a need has been felt for providing an apparatus and method which overcomes the problems cited above.

SUMMARY OF THE INVENTION

It is therefore an object of the present invention to provide an improved portable, adjustable, pneumatic, lumbar support that permits a user with chronic or acute back pain to select and subsequently lie in a customized neutral lumbar position so as to decrease the pain in the lumbar area.

Briefly described according to one embodiment of the present invention, a portable, adjustable, pneumatic, lumbar support is disclosed, designed as a portable device that facilitates manual adjustment of the user to create a posterior pelvic tilt, placing the lumbar region into a natural, neutral position, alleviating lower back pain by strengthening superficial muscles. The present invention rests on the ground or floor, and allows the user to perform pelvic tilt exercises and to apply heat or cold therapy to the vertebrae of the spine. Thus, the present invention implements proper body positioning through proper alignment of the lower lumbar region.

The present invention comprises a lower back pad, upon which a user places his or her upper torso, lying face-up.

A temperature control apparatus, such as a hot pack or cold pack, is located inside the lower back pad, corresponding and covering approximately the area between the T-4 and L-5 vertebrae of the user when lying on the mid to lower back extremity.

A leg-raising cushion, of a generally rectangular, block shape configuration, rests flush against the floor, and is used to raise the user's legs such that the thighs are oriented approximately 45–90 degrees upward in relation to the torso, depending on the height of the individual.

A hollow, inflatable bladder is located between the lower back pad and the leg-raising cushion, placing the three components in linear alignment.

The inflatable bladder contains a spinal indentation along the elongated centerline of the present invention, at the lateral midline of the inflatable bladder. The spinal indentation is constructed to permit resting of the spinal column therein, thereby reducing pressure on the spinal column from the inflatable bladder. The spinal indentation continues linearly onto the lower back pad, with the indentation conforming and corresponding to the various spinal vertebrae lying on the lower back pad during use of the present invention.

Gripping protrusions are located on the upper, exterior surface of the inflatable bladder, and are designed to reduce downward sliding of the buttocks and to create a slight distraction of lower vertebrae on the inflatable bladder during inflation of the inflatable bladder.

The leg-raising cushion is releasably secured to the inflatable bladder via component securement means. The leg-raising cushion is detachable into three areas to serve as an exercise cushion.

When a user is positioned on the present invention, the inflatable bladder extends from the upper portion of the hamstring region of the leg to approximately the L-5 vertebrae, and is constructed such that inflation in the hamstring region causes a displacement greater than that of the buttocks region, allowing for more tilt of the lower spine. By inflating and deflating the inflatable bladder, the user can cause an anterior and posterior pelvic tilt, exercising and stretching the lumbar vertebrae and muscles. The user can also adjust the inflatable bladder so that the comfortable, normal resting position is achieved.

Pneumatic pressure to the inflatable bladder is provided by a portable electric air compressor. The electric air compressor may be remotely controlled by the user via a compressor control pad. The air compressor is powered by batteries, but traditional AC power is also envisioned.

Securement means extend from either side of the present invention, and are of sufficient length to wrap around a user's abdomen in the center of the lumbar region. Thus, the securement means secures the user to the present invention in order to ensure an effective treatment and to increase minimal distraction as the pelvic tilt is being performed.

It is another object of the present invention to provide a device that produces proper leg position to support the lumbar region.

It is another object of the present invention to provide a device that is detachably secured to the waist of the user.

It is another object of the present invention to provide a device that produces pelvic stretching and exercise.

It is another object of the present invention to provide a device that is pneumatically operated.

It is another object of the present invention to provide a device that strengthens the lumbar region.

It is another object of the present invention to provide a device that is affordable.

It is another object of the present invention to provide a device that is easily stored when not in use.

It is another object of the present invention to provide a device that can easily be used at home, office or other desired location.

It is another object of the present invention to provide a device that trains muscle memory to facilitate proper spinal alignment.

It is another object of the present invention to provide a device that provides soothing comfort and soreness reduction via a heating pad.

It is another object of the present invention to provide an education to the individual for better understanding of their duty of examining proper positioning of the lower back and how to perform a correct posterior pelvic tilt.

Descriptive Key 10 portable, adjustable, pneumatic, lumbar support
15 lumbar region
20 lower back pad
40 leg-raising cushion
45 leg raising cushion securement means
60 inflatable bladder
70 spinal indentation
80 gripping protrusion
90 component securement means
93 hamstring
95 leg
97 buttocks
100 air compressor
110 air compressor control pad
120 securement means
130 temperature control apparatus
135 hot pack and/or cold pack
140 air channel

BRIEF DESCRIPTION OF THE DRAWINGS

The advantages and features of the present invention will become better understood with reference to the following more detailed description and claims taken in conjunction with the accompanying drawings, in which like elements are identified with like symbols, and in which:

DESCRIPTION OF THE PREFERRED EMBODIMENTS

The best mode for carrying out the invention is presented in terms of its preferred embodiment, herein depicted within the FIGS. 1 through 6c.

1. Detailed Description of the Figures

Figure 1:
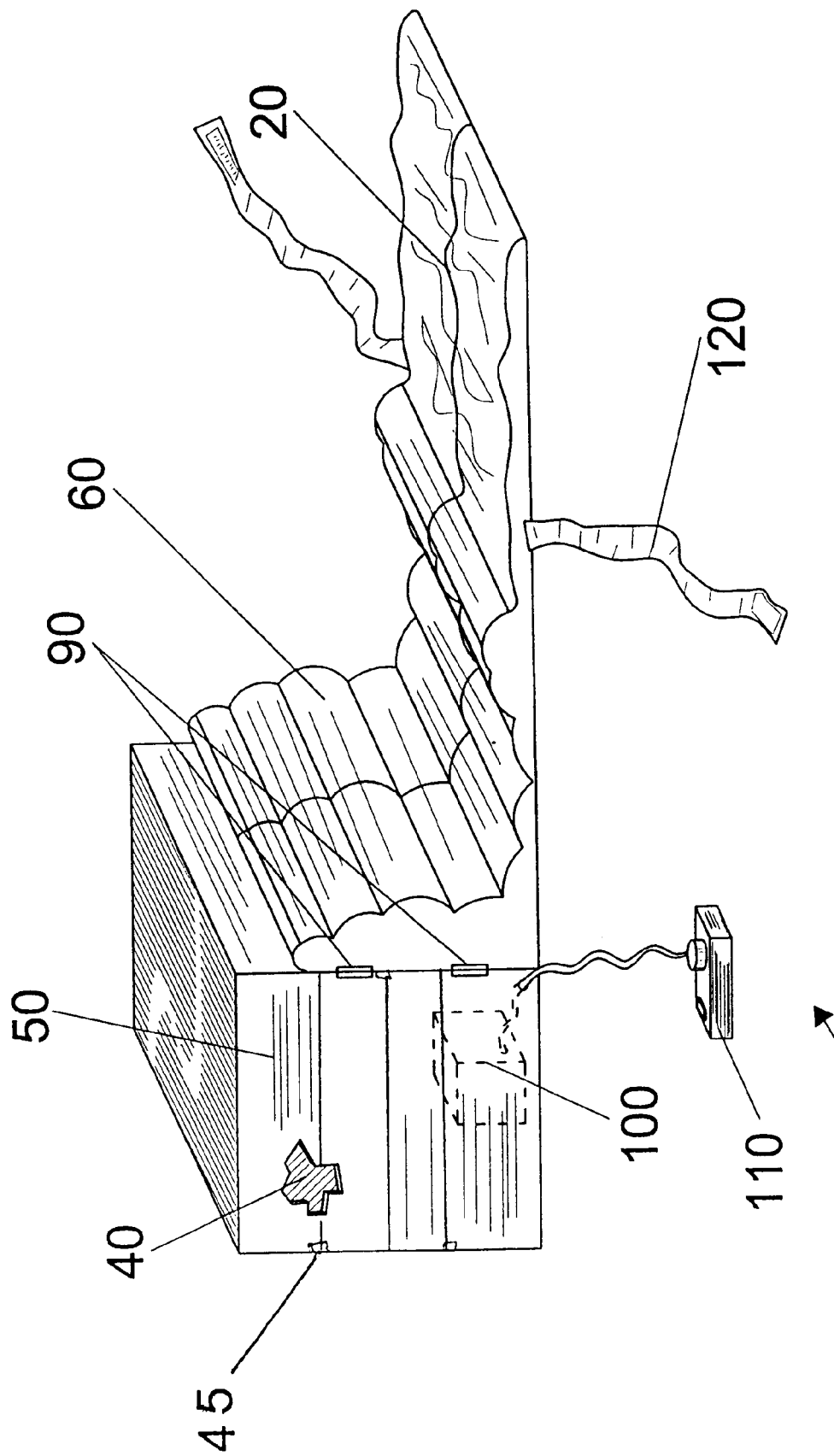
FIG. 1 is a perspective view of the preferred embodiment of a portable, adjustable, pneumatic, lumbar support 10.
Figure 2:
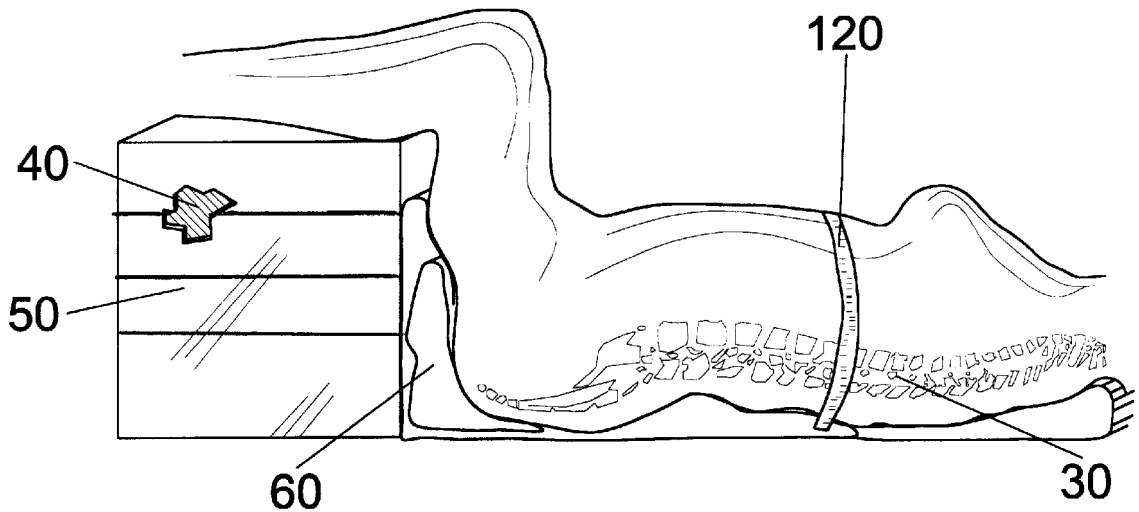
FIG. 2 is a perspective view thereof in-use showing a spinal column.

Referring now to FIGS. 1 and 2, a portable, adjustable, pneumatic, lumbar support 10 is shown, according to the present invention, is designed to permit a user with chronic or acute back pain to select and subsequently lie in a customized neutral lumbar position so as to decrease the pain in the lumbar area 15.

Briefly described according to one embodiment of the present invention, a portable, adjustable, pneumatic, lumbar support 10 is disclosed, designed as a portable device that facilitates manual adjustment of the user to create a posterior pelvic tilt, placing the lumbar region 15 into a natural, neutral position, alleviating lower back pain.

The present invention rests on the ground or floor or bed, and allows the user to perform pelvic tilt exercises and to apply heat therapy to the vertebrae of the spine. Thus, the present invention implements proper body positioning through proper alignment of the lower lumbar region 15.

Figure 3:
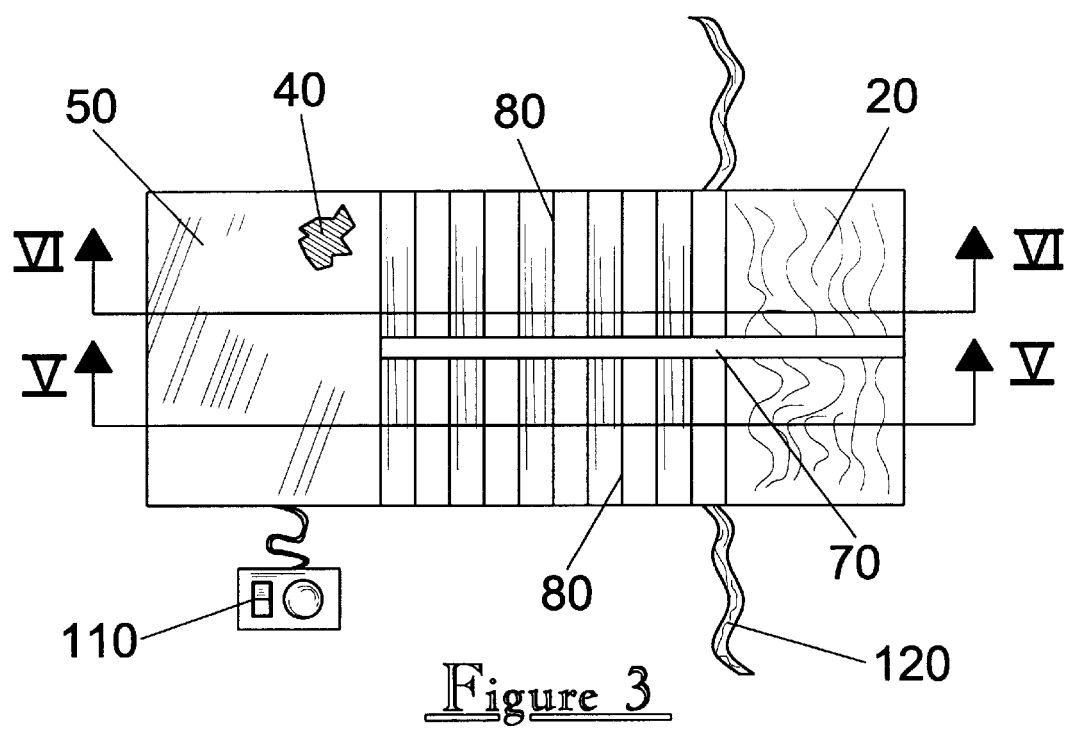
FIG. 3 is a top view thereof.

Referring now to FIGS. 1, 2, and 3, the present invention comprises a lower back pad 20, of a generally flat, horizontally elongated, rectangular configuration, upon which a user places his or her upper torso, lying face-up. It is envisioned that the lower back pad 20 is constructed of a material selected from the group comprising rubber, plastic or vinyl.

A leg-raising cushion 40, of a generally rectangular, block shape configuration, rests flush against the floor, and is used to raise the user's legs such that the thighs are oriented approximately 45–90 degrees upward in relation to the torso, depending on the height of the individual.

The leg-raising cushion 40 is separated into a plurality of areas folded together. Each area from said plurality of areas can be taken off the leg-raising cushion 40 in order to create sufficient height and exercise requirements for each individual. The leg-raising cushion 40 may be separated from the present invention and used as a floor mat or other similar device. Each piece of the leg-raising cushion is held in place via leg-raising cushion securement means 45, such as hook and loop fasteners. It is envisioned that the leg-raising cushion 40 is constructed of a material selected from the group comprising plastic, rubber or vinyl.

Referring now to FIGS. 1 through 4, a hollow, inflatable bladder 60 is located between the lower back pad 20 and the leg-raising cushion 40, placing the three components in linear alignment. It is envisioned that the inflatable bladder 60 is constructed of rubber or plastic.

Referring now to FIG. 3, the inflatable bladder 60 contains a spinal indentation 70 along the elongated centerline of the present invention, at the lateral midline of the inflatable bladder 60. The spinal indentation 70 is constructed to permit resting of the spinal column therein, thereby reducing pressure on the spinal column from the inflatable bladder 60. The spinal indentation 70 continues linearly onto the lower back pad 20, with the spinal indentation 70 conforming and corresponding to the various spinal vertebrae lying on the lower back pad 20 during use of the present invention.

Gripping protrusions 80 are located on the upper, exterior surface of the inflatable bladder 60, and are designed to reduce downward sliding of the buttocks and to create a slight distraction of lower vertebrae on the inflatable bladder 60 during inflation of the inflatable bladder 60. For purposes of disclosure, the gripping protrusions 80 consist of laterally elongated ridges protruding from the inflatable bladder 60 and extending the width of the inflatable bladder 60, equally spaced and parallel to one another.

Figure 4:
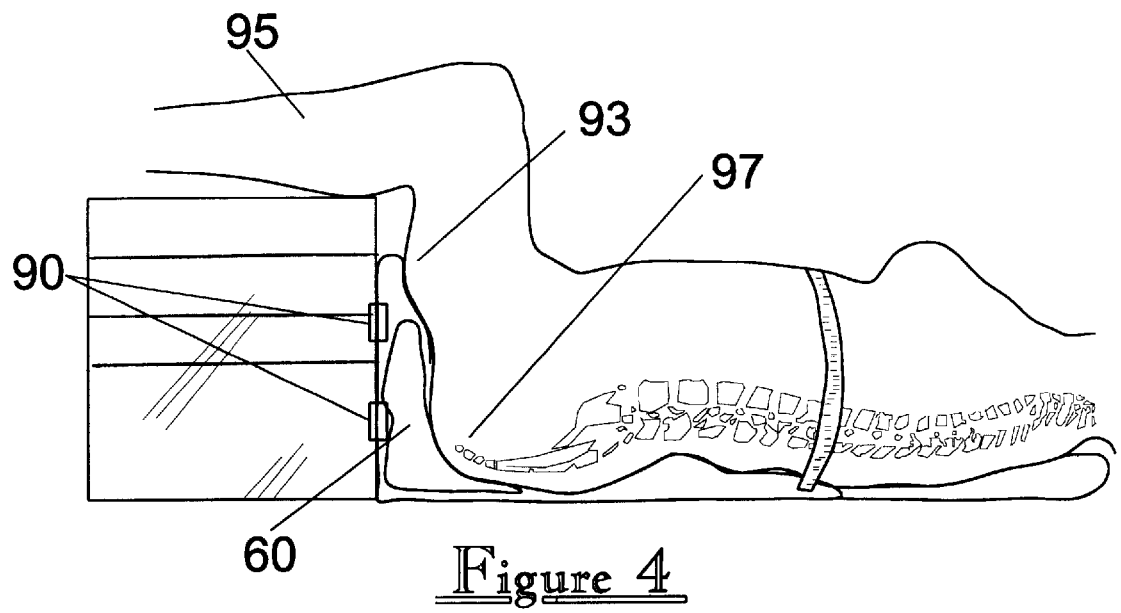
FIG. 4 is a left side view thereof.

Referring now to FIGS. 1 and 4, the leg-raising cushion 40 is releasable secured to the inflatable bladder 60 via component securement means 90. For purposes of disclosure, the component securement means 90 is depicted as fasteners of the hook and loop variety.

Referring now to FIG. 4, when a user is positioned on the present invention, the inflatable bladder 60 extends from the upper portion of the hamstring 93 region of the leg 95 to approximately the L-5 vertebrae, and is constructed such that inflation in the hamstring 93 region causes a displacement greater than that of the buttocks 97 region, allowing for more tilt of the lower spine.

Figure 5:
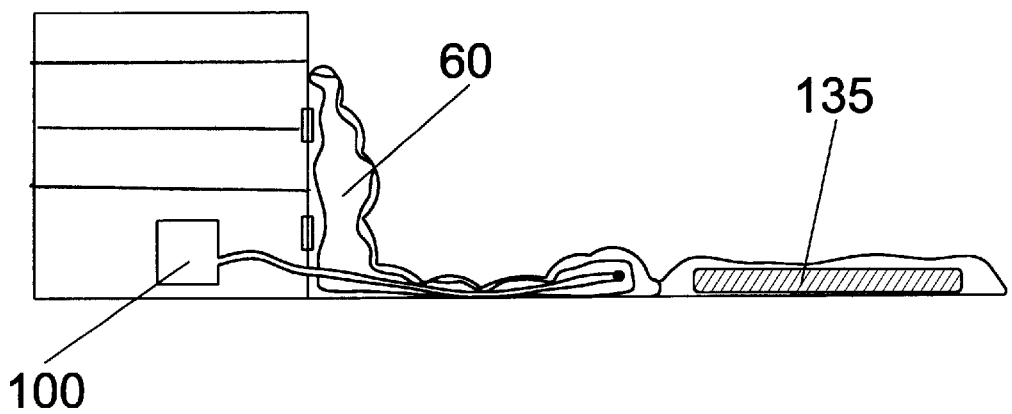
FIG. 5 is a cross-sectional view thereof, cut along line V—V of FIG. 3.

Referring now to FIGS. 5, pneumatic pressure to the inflatable bladder 60 is provided by a portable electric air compressor 100.

Referring now to FIGS. 1, 3 and 5, the electric air compressor 100 may be remotely controlled by the user via an air compressor control pad 110. The air compressor 100 is powered by batteries, but traditional AC power is also envisioned. Securement means 120 extend from either side of the present invention, and are of sufficient length to wrap around a user's abdomen in the center of the thoracic region. Thus, the securement means 120 secure the user to the present invention in order to ensure an effective treatment by slight distraction of the spinal column. For purposes of disclosure, the securement means 120 is depicted as straps utilizing fasteners of the hook and loop variety.

Referring now to FIG. 5, a temperature control apparatus 130 is located inside the lower back pad 20, corresponding and covering approximately the area between the T-4 and L-5 vertebrae of the user when lying on the lower back pad 20. For purposes of disclosure, the temperature control means 130 is depicted as a hot pack and/or a cold pack 135.

The cold pack assists in slowing the blood down to an affected area for more nutrient building. The body's response is to send endorphins to the affected region. As the ice slows the blood flow, and then as body warms in that area, more nutrients are taken away and replenished.

Figure 6A:
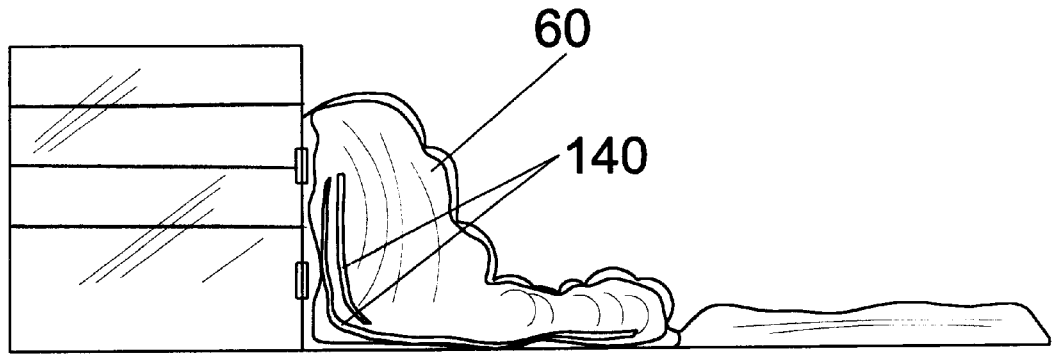
FIGS. 6a–6c are a series of cross sectional views cut along line VI—VI of FIG. 3, showing the inflatable bladder in various stages of inflation.
Figure 6B:
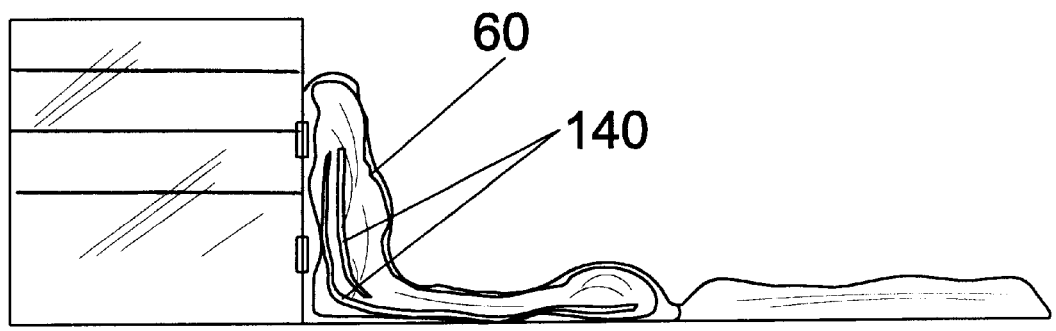
Figure 6C:
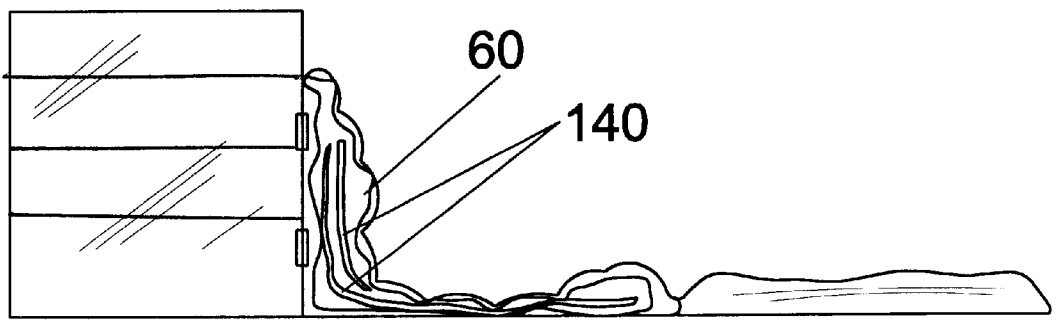

Referring now to FIGS. 6a–6c, by inflating and deflating the inflatable bladder 60, the user can cause a slight anterior, but mostly posterior pelvic tilt, exercising and stretching the lumbar 15 vertebrae and muscles. The user can also adjust the inflatable bladder 60 so that the comfortable, normal resting position is achieved.

The inflatable bladder 60 has air channels 140 which permit air to enter the inflatable bladder 60 and inflate the inflatable bladder 60 in a specific sequence. The air enters the inflatable bladder 60 starting at a position approximating the position of the L5 vertebrae when the user in on the present invention. The air influx is in a generally horizontal pattern. The air is then channeled to increase the inflatable bladder 60 vertically creating a C-type inflation configuration. Air would then increase mostly in the hamstring 93 area and some in the buttocks 97 region. This inflation sequence is important to ensure proper distraction and tilt of the spine.

It is envisioned that other styles and configurations of the present invention can be easily incorporated into the teachings of the present invention, and only one particular configuration shall be shown and described for purposes of clarity and disclosure and not by way of limitation of scope.

2. Operation of the Preferred Embodiment

To use the present invention, the operator is in the prone position on the lower back pad 20, face up. The legs are placed on the leg-raising cushion 40, and the operator slides his or her buttocks 97 up against the inflatable bladder 60. Next, the operator uses the air compressor control pad 110 to regulate the amount of air entering the inflatable bladder 60 until a comfortable, neutral position is reached. The hot pack and/or cold pack may be used to provide additional comfort.

The foregoing description is included to illustrate the operation of the preferred embodiment and is not meant to limit the scope of the invention. The scope of the invention is to be limited only by the following claims.

What is claimed is:

1. A portable, adjustable, pneumatic, lumbar support for use on a floor, comprising:

a lower back pad, of a generally flat, horizontally elongated, rectangular configuration, upon which a user places his or her upper torso, lying face-up during use;

a temperature control apparatus, said temperature control apparatus located inside said lower back pad;

a leg-raising cushion, of a generally rectangular, block shape configuration, said leg-raising cushion resting flush against the floor during use;

a hollow, inflatable bladder, said hollow, inflatable bladder having a lateral midline and located between said lower back pad and said leg-raising cushion, placing said inflatable bladder, said lower back pad, and said leg raising cushion in linear alignment;

component securement means, said component securement means used to releasably secure said leg-raising cushion to said inflatable bladder;

at least one portable electric air compressor, said air compressor located in said leg-raising cushion, and used to provide pneumatic pressure to said inflatable bladder;

an air compressor control pad, said air compressor control pad used to remotely control said electric air compressor; and securement means, said securement means extending from either side of the portable, adjustable, pneumatic lumbar support, and are of sufficient length to wrap around and secure to a user's abdomen in the center of the lumbar region.

2. The portable, adjustable, pneumatic, lumbar support described in claim 1, wherein said inflatable bladder further comprises:

a spinal indentation, said spinal indentation located along an elongated centerline of the support portable, adjustable, pneumatic lumbar support, at a lateral midline of said inflatable bladder, the spinal indentation constructed to permit resting of the spinal column therein, thereby reducing pressure on the spinal column from said inflatable bladder; and a plurality of gripping protrusions, said gripping protrusions located on the upper, exterior surface of said inflatable bladder, and designed to reduce downward sliding of the buttocks on said inflatable bladder during inflation of said inflatable bladder.

3. The portable, adjustable, pneumatic, lumbar support of claim 2, wherein said spinal indentation continues linearly onto said lower back pad, with said indentation conforming and corresponding to the various spinal vertebrae lying on said lower back pad during use of said present invention.

4. The portable, adjustable, pneumatic, lumbar support described in claim 1, wherein when the user is positioned on said portable, adjustable, pneumatic lumbar support, said inflatable bladder extends from the upper portion of the hamstring region of the leg to approximately the L-5 vertebrae.

5. The portable, adjustable, pneumatic lumbar support described in claim 1, wherein said inflatable bladder is constructed such that inflation in the hamstring region of the leg causes a displacement greater than that of the buttocks region of the user, allowing for more tilt of the lower spine.

6. The portable, adjustable, pneumatic, lumbar support described in claim 1, wherein by inflating and deflating said inflatable bladder, the user can cause an anterior and posterior pelvic tilt, thereby exercising and stretching the lumbar vertebrae and muscles.

7. The portable, adjustable, pneumatic, lumbar support described in claim 1, wherein said leg-raising cushion is used to raise the user's legs such that the thighs are oriented approximately 45–90° degrees upward in relation to the torso, depending on the height of the user.

8. The portable, adjustable, pneumatic, lumbar support described in claim 1, wherein said support is designed as a portable device that facilitates manual adjustment of the user to create a posterior pelvic tilt, placing the lumbar region into a natural, neutral position, alleviating lower back pain.

9. The portable, adjustable, pneumatic, lumbar support described in claim 1, wherein said temperature control means consists of a hot pack and cold pack.

10. The portable, adjustable, pneumatic, lumbar support described in claim 1, wherein said temperature control apparatus corresponds and covers approximately the area between the T-4 and L-5 vertebrae of the user when lying on said lower back pad.

11. The portable, adjustable, pneumatic, lumbar support described in claim 1, wherein said inflatable bladder is constructed of rubber or plastic.

12. The portable, adjustable, pneumatic, lumbar support described in claim 1, wherein said leg-raising cushion may be separated into a plurality of areas folded together, each area from said plurality of areas can be taken off said leg-raising cushion in order to create sufficient height and exercise requirements for each individual user.

13. The portable, adjustable, pneumatic, lumbar support described in claim 1, wherein said leg-raising cushion may be separated from the present invention and used as a floor mat or other similar device.

* * * * *